United States Patent
Kawano et al.

(10) Patent No.: US 9,587,228 B2
(45) Date of Patent: Mar. 7, 2017

(54) VECTOR CONTAINING A DNA CODING FOR A NOVEL GLUCOSE DEHYDROGENASE AND METHOD

(71) Applicant: Kaneka Corporation, Osaka-Shi, Osaka (JP)

(72) Inventors: Shigeru Kawano, Takasago (JP); Yoshihiko Yasohara, Takasago (JP)

(73) Assignee: KANEKA CORPORATION, Osaka (JP)

( * ) Notice: Subject to any disclaimer, the term of this patent is extended or adjusted under 35 U.S.C. 154(b) by 0 days.

(21) Appl. No.: 15/051,813

(22) Filed: Feb. 24, 2016

(65) Prior Publication Data

US 2016/0168544 A1    Jun. 16, 2016

Related U.S. Application Data

(62) Division of application No. 12/680,050, filed as application No. PCT/JP2008/067154 on Sep. 24, 2008.

(30) Foreign Application Priority Data

Sep. 26, 2007  (JP) ................. 2007-249118
Feb. 19, 2008  (JP) ................. 2008-037811

(51) Int. Cl.

| | |
|---|---|
| *C07H 21/00* | (2006.01) |
| *C12Q 1/02* | (2006.01) |
| *C12Q 1/32* | (2006.01) |
| *C12Q 1/54* | (2006.01) |
| *C12N 1/21* | (2006.01) |
| *C12N 15/70* | (2006.01) |
| *C12N 15/74* | (2006.01) |
| *C12N 9/04* | (2006.01) |
| *C12Q 1/00* | (2006.01) |

(52) U.S. Cl.
CPC .......... *C12N 9/0006* (2013.01); *C12Q 1/006* (2013.01); *C12Q 1/32* (2013.01); *C12Q 1/54* (2013.01); *C12Y 101/01047* (2013.01)

(58) Field of Classification Search
CPC ............................. C12N 9/0006; C12Q 1/006
See application file for complete search history.

(56) References Cited

U.S. PATENT DOCUMENTS 6,740,215 B1    5/2004  Nakaminami et al.
2008/0038803 A1  2/2008  Iwasaki et al.

FOREIGN PATENT DOCUMENTS

| JP | 63-109773 A | 5/1988 |
|---|---|---|
| JP | 2006-262767 A | 10/2006 |
| WO | WO-2006090814 A1 | 8/2006 |

OTHER PUBLICATIONS

Extended Europen Search Report dated Oct. 13, 2010 for corresponding EP Application No. 08833102.0.
Adachi et al., Crystallization and Characterization of NADP-Dependent D-Glucose Dehydrogenase from Gluconobacter suboxydans, Agric. Biol. Chem., 44(2), 301-308, 1980.
Weckbecker et al., Clucose Dehydrogenase for the Regeneration of NADPH and NADH, Methods in Biotechnology, vol. 17, 2005, pp. 225-237.
Eguchi et al., NADPH Regeneration by Glucose Dehydrogenase from Gluconobacter scleroides fro I-Leucovorin Synthesis, Biosci. Biotech. Biochem., 56 (5), 701-703, 1992.
Database uniport [Online], Databse accession No. Q03HY8 (2006).
Database uniprot [Online], Database accession No. Q036E5 (2006).
Database uniprot [Online], Database accession No. Q1WVF6 (2006).
Database uniprot [Online], Database accession No. Q5FK32 (2005).
Lee et al., Oxidative Metabolism in Pediococcus pentosaceus, Journal of Bacteriology, vol. 90, No. 3, Sep. 1965, pp. 653-660.
Settanni et al., "Rapid Differentiation and In Sity Detection of 16 Sourdough *Lactobacillus* Species by Multiplex PCR", Applied and Environmental Microbiology, vol. 71, No. 6, Jun. 2005, pp. 3049-3059.
Yasohara, Bio Fuei Kangen System, Kagaku to Seibutsu, 2006, vol. 44, No. 9, pp. 629-632.
English translation of International Preliminary Report on Patentability (Chapter I) in PCT/JP2008/067154.
Ausubel, F., Current Protocols in Molecular Biology, Hybridization Analysis of DNA Blots, pp. 2.10.8-2.10.11.
Branden et al., Introduction to Protein Structure, Garland Publishing Inc., New York, p. 247, 1991.
Witkowski et al., Biochemistry 38:11643-11650, 1999.
Seffernick et al., J. Bacteriol. 183(8):2405-2410, 2001.
D'Souza, S.F., Biosensors and Bioelectronics 16:337-353, 2001.
Tzang et al., Biosensors and Bioelectronics 16:211-219, 2001.

*Primary Examiner* — Delia Ramirez
(74) *Attorney, Agent, or Firm* — Polsinelli PC

(57) ABSTRACT

The invention relates to a glucose dehydrogenase showing an NADP/NAD activity ratio, namely the value obtained by dividing the enzyme activity value obtained by using NADP as a coenzyme by the enzyme activity value obtained by using NAD as a coenzyme, of not lower than 300, to a gene coding therefor, and to a transformant harboring that gene. The enzyme of the invention is very high in NADP specificity and can be suitably used, for example, for NADPH production, for coenzyme regeneration in enzymatic reduction reactions, and in biosensors for glucose concentration measurements.

7 Claims, No Drawings

VECTOR CONTAINING A DNA CODING FOR A NOVEL GLUCOSE DEHYDROGENASE AND METHOD

CROSS REFERENCE TO RELATED APPLICATIONS

This application is a Divisional of U.S. application Ser. No. 12/680,050 filed on Mar. 35, 2010, now U.S. Pat. No. 9,303,280 which is a National Phase filing under 35 U.S.C. §371 of PCT/JP2008/067154 filed Sep. 24, 2008, which claims priority to Japanese Patent Application number 2007-249118 filed on Sep. 26, 2007 and Japanese Patent Application number 2008-037811 filed on Feb. 19, 2008. The entire contents of each of the above-applications are incorporated herein by reference.

TECHNICAL FIELD

The present invention relates to a novel glucose dehydrogenase, a gene therefor, a vector containing the gene, a transformant as transformed with the vector, and a reduction reaction system utilizing the same.

BACKGROUND ART

Glucose dehydrogenases are enzymes catalyzing the reaction in which glucose and oxidized nicotinamide adenine dinucleotide (hereinafter, NAD) or oxidized nicotinamide adenine dinucleotide phosphate (hereinafter, NADP) are converted to D-δ-gluconolactone (hereinafter, gluconolactone) and reduced nicotinamide adenine dinucleotide (hereinafter, NADH) or reduced nicotinamide adenine dinucleotide phosphate (hereinafter, NADPH). These glucose dehydrogenases are widely distributed in various organisms, from bacteria and yeasts to mammals, and many of them show activity in cooperation with both NAD and NADP as coenzymes.

On the other hand, NADP-specific glucose dehydrogenases are industrially useful enzymes utilizable in biosensors or as coenzyme-regenerating enzymes in NADP-specific dehydrogenase-based reduction reactions, each making the best use of the NADP-specific feature thereof. As regards the use thereof in biosensors, a high-sensitivity method of assaying NADPH utilizing an NADPH oxidase and glucose-6-phosphate dehydrogenase (to be described later herein) has been reported (Non-Patent Document 1). Further, International Publication WO 2006/090814 describes a method of producing optically active secondary alcohols, according to which an enantiomer mixture of a secondary alcohol is converted to an optically active secondary alcohol substantially consisting of a single enantiomer; for efficient production of optically active secondary alcohols, however, it is desired that the NADP-specific glucose dehydrogenase to be used show an NADP/NAD activity ratio as high as possible (Patent Document 1).

Known glucose dehydrogenases specifically acting on the coenzyme NADP are ones derived from the genera *Cryptococcus*, *Gluconobacter* and *Saccharomyces* (cf. Patent Documents 2 and 3 and Non-Patent Documents 2 and 3). Only for the *Cryptococcus uniguttulatus* JCM 3687 strain-derived NADP-specific glucose dehydrogenase, among them, information concerning the amino acid sequence and the enzyme-encoding DNA sequence has been obtained. Thus, the number of known NADP-specific glucose dehydrogenases is small and only scanty relevant amino acid sequence and encoding DNA sequence information is available. Accordingly, it has been desired for novel NADP-specific glucose dehydrogenases as well as information about the base sequences encoding the enzymes and information about the amino acid sequences of the enzymes to be provided.

On the other hand, as other examples of the enzymes specifically acting on NADP as a coenzyme, there are glucose-6-phosphate dehydrogenases. It is known that certain glucose-6-phosphate dehydrogenases derived, for example, from the genera *Cryptococcus*, *Aspergillus* and *Pseudomonas*, among others, are active with glucose as well and therefore have NADP-specific glucose dehydrogenating activity. However, their glucose dehydrogenase activity is at most 15% as compared with their glucose-6-phosphate dehydrogenase activity (Non-Patent Document 4), so that they are not suited for use as glucose dehydrogenases. Therefore, for efficiently reducing NADP to NADPH using glucose-6-phosphate dehydrogenases, glucose-6-phosphate, which is expensive, is required; such a method cannot be said economical.

The glucose dehydrogenase activity of bacteria belonging to the genus *Lactobacillus* was studied in the past; it is reported that they have no such activity (Non-Patent Document 5). Further, polypeptides derived from the *Lactobacillus acidophilus* NCFM strain and *Lactobacillus salivarius* subsp. *salivarius* UCC 118 strain have been registered as *Lactobacillus* bacterial glucose dehydrogenases in the gene database GenBank. However, no report has yet been made about experimental confirmation that either of the polypeptides has or fails to have glucose dehydrogenase activity. In this way, it may be said that there is no report at all about glucose dehydrogenases of bacteria belonging to the genus *Lactobacillus*.

As for the glucose dehydrogenase activity of bacteria belonging to the genus *Pediococcus*, a report says that *Pediococcus pentosaceus* and *Pediococcus cerevisiae* have that enzyme activity (Non-Patent Document 5). However, there is no report about the NADP specificity thereof.

Patent Document 1: International Publication WO 2006/090814

Patent Document 2: Japanese Patent Publication (Kokoku) S63-109773

Patent Document 3: Japanese Kokai Publication 2006-262767

Non-Patent Document 1: Hokkaido Industrial Research Institute Report, Vol. 293, pp. 141-145, 1994

Non-Patent Document 2: J. Bacteriol., Vol. 184, No. 3, pp. 672-678, 2002

Non-Patent Document 3: Methods Enzymol., Vol. 89, pp. 159-163, 1982

Non-Patent Document 4: Arch. Biochem. Biophys., Vol. 228, No. 1, pp. 113-119, 1984

Non-Patent Document 5: J. Bacteriol., Vol. 90, No. 3, pp. 653-660, 1965

SUMMARY OF THE INVENTION

An object of the present invention is to provide a novel glucose dehydrogenase specifically acting on NADP and a method of utilizing the same.

To accomplish the above object, the present inventors performed a screening for novel glucose dehydrogenases specifically acting on NADP. As a result, they could find out, from among lactic acid bacteria, a novel glucose dehydrogenase higher in NADP specificity as compared with the NADP-specific glucose dehydrogenases so far reported.

And, they also succeeded in causing high-level expression of that enzyme by introducing the relevant gene of that enzyme into host organisms.

The present invention has one or a plurality of the following features.

In an aspect thereof, the invention relates to a glucose dehydrogenase specifically acting on NADP, which is derived from lactic acid bacteria, in particular from bacteria of the genus *Lactobacillus* or *Pediococcus*.

In another aspect, the invention relates to a glucose dehydrogenase specifically acting on NADP, which is derived from lactic acid bacteria, in particular from bacteria of the genus *Lactobacillus* or *Pediococcus*, and is a polypeptide selected from the group consisting of the polypeptides (a1), (a2), (a3), (b1), (b2), (b3), (c1), (c2) and (c3) specified below:

(a1) a polypeptide having the amino acid sequence described in the sequence listing under SEQ ID NO:1;

(a2) polypeptides having an amino acid sequence derived from the amino acid sequence described in the sequence listing under SEQ ID NO:1 by substitution, deletion, insertion and/or addition of one or a plurality of amino acid residues and capable of acting on glucose and NADP to form gluconolactone and NADPH;

(a3) polypeptides having a sequence homology of at least 90% with the amino acid sequence described in the sequence listing under SEQ ID NO:1 and capable of acting on glucose and NADP to form gluconolactone and NADPH;

(b1) a polypeptide having the amino acid sequence described in the sequence listing under SEQ ID NO:3;

(b2) polypeptides having an amino acid sequence derived from the amino acid sequence described in the sequence listing under SEQ ID NO:3 by substitution, deletion, insertion and/or addition of one or a plurality of amino acid residues and capable of acting on glucose and NADP to form gluconolactone and NADPH;

(b3) polypeptides having a sequence homology of at least 85% with the amino acid sequence described in the sequence listing under SEQ ID NO:3 and capable of acting on glucose and NADP to form gluconolactone and NADPH;

(c1) a polypeptide having the amino acid sequence described in the sequence listing under SEQ ID NO:11;

(c2) polypeptides having an amino acid sequence derived from the amino acid sequence described in the sequence listing under SEQ ID NO:11 by substitution, deletion, insertion and/or addition of one or a plurality of amino acid residues and capable of acting on glucose and NADP to form gluconolactone and NADPH;

(c3) polypeptides having a sequence homology of at least 85% with the amino acid sequence described in the sequence listing under SEQ ID NO:11 and capable of acting on glucose and NADP to form gluconolactone and NADPH.

In another aspect, the present invention relates to a DNA which is any of the following (A1) to (A4):

(A1) a DNA having the base sequence shown in the sequence listing under SEQ ID NO:2;

(A2) a DNA coding for a polypeptide having the amino acid sequence described in the sequence listing under SEQ ID NO:1;

(A3) a DNA hybridizing with a DNA having a base sequence complementary to the base sequence shown in the sequence listing under SEQ ID NO:2 under stringent conditions and coding for a polypeptide acting on glucose and NADP to form gluconolactone and NADPH;

(A4) a DNA having a sequence homology of at least 90% with the base sequence shown in the sequence listing under SEQ ID NO:2 and coding for a polypeptide acting on glucose and NADP to form gluconolactone and NADPH.

In another aspect, the present invention relates to a DNA which is any of the following (B1) to (B4):

(B1) a DNA having the base sequence shown in the sequence listing under SEQ ID NO:4;

(B2) a DNA coding for a polypeptide having the amino acid sequence described in the sequence listing under SEQ ID NO:3;

(B3) a DNA hybridizing with a DNA having a base sequence complementary to the base sequence shown in the sequence listing under SEQ ID NO:4 under stringent conditions and coding for a polypeptide acting on glucose and NADP to form gluconolactone and NADPH;

(B4) a DNA having a sequence homology of at least 85% with the base sequence shown in the sequence listing under SEQ ID NO:4 and coding for a polypeptide acting on glucose and NADP to form gluconolactone and NADPH.

In another aspect, the present invention relates to a DNA which is any of the following (C1) to (C4):

(C1) a DNA having the base sequence shown in the sequence listing under SEQ ID NO:12;

(C2) a DNA coding for a polypeptide having the amino acid sequence described in the sequence listing under SEQ ID NO:11;

(C3) a DNA hybridizing with a DNA having a base sequence complementary to the base sequence shown in the sequence listing under SEQ ID NO:12 under stringent conditions and coding for a polypeptide acting on glucose and NADP to form gluconolactone and NADPH;

(C4) a DNA having a sequence homology of at least 85% with the base sequence shown in the sequence listing under SEQ ID NO:12 and coding for a polypeptide acting on glucose and NADP to form gluconolactone and NADPH.

In another aspect, the present invention relates to a method of producing NADPH which comprises using the glucose dehydrogenase of the present invention or the transformant with the DNA of the present invention introduced therein or a processed material thereof for the formation of NADPH from NADP and glucose.

In another aspect, the present invention relates to a reduction reaction system for an enzymatic reduction reaction using a reductase source requiring NADPH as a coenzyme, wherein NADPH is regenerated using the glucose dehydrogenase of the present invention or the transformant with the DNA of the present invention introduced therein or a processed material thereof.

In another aspect, the present invention relates to a biosensor for detecting compounds, wherein the glucose dehydrogenase of the present invention or the transformant with the DNA of the present invention introduced therein is used.

The present invention provides a novel glucose dehydrogenase, a gene therefor, a vector containing that gene, a transformant as transformed with that vector, a method of producing NADPH utilizing them, and a reduction reaction system utilizing them.

BEST MODE FOR CARRYING OUT THE INVENTION

In the following, the invention is described in detail referring to typical modes of embodiment thereof. However, these modes of embodiment are by no means limitative of the scope of the invention.

The glucose dehydrogenase of the invention is a glucose dehydrogenase specifically acting on NADP as a coenzyme (NADP-specific glucose dehydrogenase). This aspect is described below.

Re: Specificity for NADP

The phrase "specifically acting on NADP" as used herein refers to the fact that the enzyme virtually does not act on NAD but acts only on NADP. This means that when the glucose dehydrogenase activity is measured by the enzyme activity measurement method described below using NAD or NADP and the enzyme activity value obtained by using NADP is divided by the enzyme activity value obtained by using NAD, the ratio (NADP/NAD activity ratio) is not lower than 300. Preferably, the NADP/NAD activity ratio is not lower than 500, more preferably not lower than 1000, still more preferably not lower than 5000, most preferably not lower than 10000.

[Glucose Dehydrogenase Activity Measurement Method]

The progress of the oxidation reaction of glucose to gluconolactone can be evaluated with ease by allowing the reaction to proceed in a reaction mixture containing 2.0 mM NAD or NADP and 100 mM glucose and a glucose dehydrogenase to be evaluated in 1.0 M Tris-hydrochloride buffer (pH 8.0) at 25° C. and measuring the increase in absorbance at the wavelength 340 nm as resulting from the increase in the amount of NADH or NADPH. One unit (1 U) of glucose dehydrogenase activity was defined as the enzyme amount catalyzing the formation of 1 μmol (micromole) of NADH or NADPH in one minute.

Re: Isolation of the Glucose Dehydrogenase of the Invention

The glucose dehydrogenase of the invention can be isolated from lactic acid bacteria having the activity in question, in particular from bacteria belonging to the genus *Lactobacillus* or *Pediococcus*. Lactic acid bacteria containing that enzyme can be found out, for example, by the following method.

Lactic acid bacteria are cultured on an appropriate medium, and bacterial cells are collected from the culture fluid by centrifugation or filtration. The cells obtained are disrupted by physical means, for example by the use of a sonicator or glass beads, and the cell debris is then removed by centrifugation to give a cell-free extract. The extract can be evaluated with ease as to whether it contains a NADP-specific glucose dehydrogenase or not by measuring the activity values for the cases where NAD and NADP are used respectively by the glucose dehydrogenase activity measurement method described hereinabove.

Usable as the medium for culturing the lactic acid bacteria are ordinary nutrient broths containing carbon and nitrogen sources, inorganic salts, organic nutrients and so forth provided that the lactic acid bacteria can grow on the medium selected; thus, for example, MRS medium can be used. The cultivation can be carried out, for example, in the manner of stationary culture under anaerobic conditions at a temperature of 25° C. to 37° C.

The enzyme in question can be isolated from lactic acid bacteria by an appropriate combination of known techniques for protein purification. For example, the isolation can be carried out in the following manner. First, the *Lactobacillus* bacteria are cultured on an appropriate medium, and cells are collected from the culture fluid by centrifugation or filtration, for instance. The cells obtained are disrupted by physical means, for example by using a sonicator or glass beads, and the cell debris is then removed by centrifugation to give a cell-free extract. And, the glucose dehydrogenase according to the invention is isolated from the cell-free extract by using such techniques as heat treatment, salting out (e.g. precipitation with ammonium sulfate or sodium phosphate), solvent precipitation (fractional protein precipitation with acetone or ethanol, for instance), dialysis, gel filtration chromatography, ion exchange chromatography, reversed phase chromatography and ultrafiltration, applied either singly or in combination.

The origin of the glucose dehydrogenase of the invention is not particularly restricted but is to be one derived from among lactic acid bacteria. Preferred are, however, bacteria belonging to the genus *Lactobacillus* or *Pediococcus*.

Examples of the bacteria belonging to the genus *Lactobacillus* include *Lactobacillus acetotolerans*, *Lactobacillus acidipiscis*, *Lactobacillus acidophilus*, *Lactobacillus agilis*, *Lactobacillus algidus*, *Lactobacillus alimentarius*, *Lactobacillus amylolyticus*, *Lactobacillus amylophilus*, *Lactobacillus amylotrophicus*, *Lactobacillus amylovorus*, *Lactobacillus animalis*, *Lactobacillus arizonensis*, *Lactobacillus aviarius* subsp. *araffinosus*, *Lactobacillus aviarius* subsp. *aviarius*, *Lactobacillus bavaricus*, *Lactobacillus bifermentans*, *Lactobacillus brevis*, *Lactobacillus buchneri*, *Lactobacillus bulgaricus*, *Lactobacillus camelliae*, *Lactobacillus casei*, *Lactobacillus casei* subsp. *alactosus*, *Lactobacillus casei* subsp. *casei*, *Lactobacillus casei* subsp. *pseudoplantarum*, *Lactobacillus casei* subsp. *rhamnosus*, *Lactobacillus casei* subsp. *tolerans*, *Lactobacillus catenaformis*, *Lactobacillus cellobiosus*, *Lactobacillus coleohominis*, *Lactobacillus collinoides*, *Lactobacillus composti*, *Lactobacillus concavus*, *Lactobacillus confusus*, *Lactobacillus coryniformis* subsp. *coryniformis*, *Lactobacillus coryniformis* subsp. *torquens*, *Lactobacillus crispatus*, *Lactobacillus curvatus*, *Lactobacillus curvatus* subsp. *melibiosus*, *Lactobacillus cypricasei*, *Lactobacillus delbrueckii* subsp. *bulgaricus*, *Lactobacillus delbrueckii* subsp. *delbrueckii*, *Lactobacillus delbrueckii* subsp. *lactis*, *Lactobacillus diolivorans*, *Lactobacillus divergens*, *Lactobacillus durianis*, *Lactobacillus equi*, *Lactobacillus farciminis*, *Lactobacillus farraginis*, *Lactobacillus ferintoshensis*, *Lactobacillus fermentum*, *Lactobacillus fornicalis*, *Lactobacillus fructivorans*, *Lactobacillus fructosus*, *Lactobacillus frumenti*, *Lactobacillus fuchuensis*, *Lactobacillus gallinarum*, *Lactobacillus gasseri*, *Lactobacillus graminis*, *Lactobacillus halotolerans*, *Lactobacillus hamsteri*, *Lactobacillus helveticus*, *Lactobacillus heterohiochii*, *Lactobacillus hilgardii*, *Lactobacillus homohiochii*, *Lactobacillus ingluviei*, *Lactobacillus intestinalis*, *Lactobacillus jensenii*, *Lactobacillus johnsonii*, *Lactobacillus kandleri*, *Lactobacillus kefir*, *Lactobacillus kefiranofaciens*, *Lactobacillus kefiranofaciens* subsp. *kefiranofaciens*, *Lactobacillus kefiranofaciens* subsp. *kefirgranum*, *Lactobacillus kefirgranum*, *Lactobacillus kefiri*, *Lactobacillus kimchii*, *Lactobacillus kitasatonis*, *Lactobacillus lactis*, *Lactobacillus leichmannii*, *Lactobacillus lindneri*, *Lactobacillus malefermentans*, *Lactobacillus mali*, *Lactobacillus maltaromicus*, *Lactobacillus manihotivorans*, *Lactobacillus mindensis*, *Lactobacillus minor*, *Lactobacillus minutus*, *Lactobacillus mucosae*, *Lactobacillus murinus*, *Lactobacillus nagelii*, *Lactobacillus oris*, *Lactobacillus panis*, *Lactobacillus pantheris*, *Lactobacillus parabuchneri*, *Lactobacillus paracasei* subsp. *paracasei*, *Lactobacillus paracasei* subsp. *tolerans*, *Lactobacillus paracollinoides*, *Lactobacillus parafarraginis*, *Lactobacillus parakefir*, *Lactobacillus parakefiri*, *Lactobacillus paralimentarius*, *Lactobacillus paraplantarum*, *Lactobacillus pentosus*, *Lactobacillus perolens*, *Lactobacillus piscicola*, *Lactobacillus plantarum*, *Lactobacillus plantarum* subsp. *plantarum*, *Lactobacillus pontis*, *Lactobacillus psittaci*, *Lactobacillus rennini*, *Lactobacillus reuteri*, *Lactobacillus rhamnosus*, *Lactobacillus rimae*, *Lactobacillus ruminis*, *Lactobacillus sake*, *Lactobacillus sakei* subsp. *carnosus*, *Lactobacillus sakei* subsp. *sakei*, *Lactobacillus salivarius*, *Lactobacillus salivarius* subsp. *salicinius*, *Lactobacillus sanfranciscensis*, *Lactobacillus sanfrancisco*, *Lactobacillus satsumensis*, *Lactobacillus sharpeae*, *Lactobacillus* sp., *Lactobacillus suebicus*, *Lactobacillus thailandensis*, *Lactobacillus thermotolerans*, *Lactobacillus uli*, *Lactobacillus vaccinostercus*, *Lactobacillus vaginalis*, *Lactobacillus vini*, *Lactobacillus viridescens*, *Lactobacillus vitulinus*, *Lactobacillus xylosus*, *Lactobacillus yamanashiensis* subsp. *mali*, *Lactobacillus yamanashiensis* subsp. *yamanashiensis*, and *Lactobacillus zeae*. Preferably used are *Lactobacillus plantarum* and *Lactobacillus pentosus*, and more preferably used are a *Lactobacillus plantarum* JCM1149 strain and a *Lactobacillus pentosus* JCM1558 strain.

Examples of the bacteria belonging to the genus *Pediococcus* include *Pediococcus acidilactici*, *Pediococcus cellicola*, *Pediococcus damnosus*, *Pediococcus dextrinicus*, *Pediococcus halophilus*, *Pediococcus inopinatus*, *Pediococcus parvulus*, *Pediococcus pentosaceus*, *Pediococcus siamensis*, and *Pediococcus urinaeequi*. Preferably used is *Pediococcus parvulus*, and more preferably used is a *Pediococcus parvulus* JCM5889 strain.

The microorganisms mentioned above can be obtained from the RIKEN BioResource Center (JCM; 3-1-1 Koyadai, Tsukuba City, 305-0074 Ibaraki Prefecture, Japan).

Re: Polypeptide of the Invention

As the polypeptide of the invention, there may be mentioned, for example, the polypeptides defined below under (a1) to (a3).
(a1) A polypeptide having the amino acid sequence described in the sequence listing under SEQ ID NO:1;
(a2) Polypeptides having an amino acid sequence derived from the amino acid sequence described in the sequence listing under SEQ ID NO:1 by substitution, deletion, insertion and/or addition of one or a plurality of amino acid residues and capable of acting on glucose and NADP to form gluconolactone and NADPH;
(a3) Polypeptides having a sequence homology of at least 90% with the amino acid sequence described in the sequence listing under SEQ ID NO:1 and capable of acting on glucose and NADP to form gluconolactone and NADPH.

The above polypeptides (a2) and (a3) are now described in detail.

Re: Polypeptides Described Under (a2)

The polypeptides having an amino acid sequence derived from the amino acid sequence described in the sequence listing under SEQ ID NO:1 by substitution, deletion, insertion and/or addition of one or a plurality of amino acid residues can be prepared according to the known methods described in Current Protocols in Molecular Biology (John Wiley and Sons, Inc., 1989) and elsewhere, and those which are capable of acting on glucose and NADP to form gluconolactone and NADPH are all included among the polypeptides defined above.

The site or sites of the amino acid substitution, insertion, deletion and/or addition in the amino acid sequence shown in the sequence listing under SEQ ID NO:1 are not particularly restricted, but highly conserved regions should preferably be avoided. The term "highly conserved region" as used herein indicates the site at which a plurality of enzymes differing in origin, upon optimal amino acid sequence alignment for comparison, show an identical partial amino acid sequence among the plurality of sequences. The highly conserved regions can be confirmed by comparing the amino acid sequence shown under SEQ ID NO:1 with the amino acid sequences of known microorganism-derived alcohol dehydrogenases using such a tool as GENETYX.

The amino acid sequence modified by substitution, insertion, deletion and/or addition may contain only one type of modification (e.g. substitution) or two or more types of modifications (e.g. substitution and insertion).

In the case of substitution, the substituting amino acid is preferably an amino acid similar in properties to the amino acid before substitution (homologous amino acid). Those amino acids which belong to one and the same group among the groups given below are herein defined as homologous amino acids.
(Group 1: neutral nonpolar amino acids) Gly, Ala, Val, Leu, Ile, Met, Cys, Pro, Phe
(Group 2: neutral polar amino acids) Ser, Thr, Gln, Asn, Trp, Tyr
(Group 3: acidic amino acids) Glu, Asp
(Group 4: basic amino acids) His, Lys, Arg The term "plurality of amino acid residues" so referred to hereinabove means, for example, not more than 25, preferably not more than 20, more preferably not more than 15, still more preferably not more than 10, 5, 4, 3 or 2 amino acid residues.

Re: Polypeptides Described Under (a3)

Those polypeptides which have a sequence homology of at least 90% with the amino acid sequence shown in the sequence listing under SEQ ID NO:1, when capable of acting on glucose and NADP to form gluconolactone and NADPH, are also included among the polypeptides of the invention. While the polypeptides having a sequence homology of at least 90% with the amino acid sequence shown in the sequence listing under SEQ ID NO:1 are included among the polypeptides of the invention, the sequence homology is preferably not lower than 92%, more preferably not lower than 95%, still more preferably not lower than 98%, most preferably not lower than 99%.

The amino acid sequence homology is expressed by the value obtained by comparing the amino acid sequence to be evaluated with the amino acid sequence shown in the sequence listing under SEQ ID NO:1, dividing the number of sites where both the sequences show identical amino acid residues by the total number of the amino acid residues compared and further multiplying the resulting quotient by 100.

As the polypeptide of the invention, there may also be mentioned the polypeptides defined below under (b1) to (b3)
(b1) A polypeptide having the amino acid sequence described in the sequence listing under SEQ ID NO:3;
(b2) Polypeptides having an amino acid sequence derived from the amino acid sequence described in the sequence listing under SEQ ID NO:3 by substitution, deletion, insertion and/or addition of one or a plurality of amino acid residues and capable of acting on glucose and NADP to form gluconolactone and NADPH;
(b3) Polypeptides having a sequence homology of at least 85% with the amino acid sequence described in the sequence listing under SEQ ID NO:3 and capable of acting on glucose and NADP to form gluconolactone and NADPH.

The above definitions (b2) and (b3) respectively are considered in the same manner as the definitions (a2) and (a3) given above.

As the polypeptide of the invention, there may further be mentioned the polypeptides defined below under (c1) to (c3).
(c1) A polypeptide having the amino acid sequence described in the sequence listing under SEQ ID NO:11;

(c2) Polypeptides having an amino acid sequence derived from the amino acid sequence described in the sequence listing under SEQ ID NO:11 by substitution, deletion, insertion and/or addition of one or a plurality of amino acid residues and capable of acting on glucose and NADP to form gluconolactone and NADPH;

(c3) Polypeptides having a sequence homology of at least 85% with the amino acid sequence described in the sequence listing under SEQ ID NO:11 and capable of acting on glucose and NADP to form gluconolactone and NADPH.

The above definitions (c2) and (c3) respectively are considered in the same manner as the definitions (a2) and (a3) given above.

Concerning the amino acid sequences shown in the sequence listing under SEQ ID NOs: 1, 3 and 11, a homology search was made in the protein sequence database GenBank using the BLAST program. As a result, the *Pediococcus pentosaceus*-derived short chain alcohol dehydrogenase (accession number: ABJ67184) showed the highest sequence homology; 87.7% with the sequence 1, 83.9% with the sequence 3, and 83.9% with the sequence 11. Although this polypeptide is reported as a short chain alcohol dehydrogenase, the function is merely an estimation based on the sequence thereof; no report has been made as yet about an actual short chain alcohol dehydrogenase activity thereof. No report has been made either as yet about the fact that this enzyme has glucose dehydrogenase activity or has NADPH-specific glucose dehydrogenase activity.

Further, an additional amino acid sequence may be bound to the amino acid sequence described under SEQ ID NO:1, 3 or 11 provided that the resulting sequence can act on glucose and NADP to form gluconolactone and NADPH. For example, a tag, such as a histidine tag or HA tag, may be added to the polypeptide. Or, a fusion protein of the polypeptide with another protein may also be produced. Further, peptide fragments of the polypeptide may also be used if they can act on glucose and NADP to form gluconolactone and NADPH.

Re: Cloning of a DNA Coding for the Polypeptide of the Invention

The DNA coding for the polypeptide of the invention may be any one if it can express the enzyme in host cells harboring the DNA introduced therein by the method to be mentioned later herein, and it may contain an arbitrary untranslated region(s). Once the enzyme in question is obtained, the one having ordinary skill in the art will be able to obtain such a DNA from the organism serving as a source of the enzyme by a known method, for example by the method shown below.

The gene manipulation procedures mentioned later herein, such as DNA cloning, vector preparation and transformation, can be carried out by the methods described in such a monograph as Molecular Cloning, 2nd Edition (Cold Spring Harbor Laboratory Press, 1989), unless otherwise specified. The symbol "%" as used herein means "% (w/v)", unless otherwise specified.

First, the enzyme of the invention as isolated by the method described above under "Re: Isolation of the glucose dehydrogenase of the invention" is digested with an appropriate endopeptidase, and the peptide fragments formed are isolated by reversed phase HPLC. The amino acid sequences of these peptide fragments are partly or wholly determined using, for example, a model ABI 492 protein sequencer (product of Applied Biosystems).

Based on the thus-obtained amino acid sequence information, PCR (Polymerase Chain Reaction) primers for amplifying a part of the DNA coding for the polypeptide in question are synthesized. Then, a chromosomal DNA of the microorganism which is the source of the polypeptide is prepared by a conventional DNA isolation technique, for example the method of Visser et al. (Appl. Microbiol. Biotechnol., 53, 415 (2000)). The PCR is carried out using this chromosomal DNA as the template, together with the above-mentioned PCR primers, to amplify a part of the DNA coding for the polypeptide, and the base sequence thereof is determined. The base sequence determination can be carried out using, for example, an Applied Biosystems 3130xl genetic analyzer (product of Applied Biosystems).

Once a part of the base sequence of the DNA coding for the polypeptide in question is known, the whole sequence can be determined, for example, by the inverse PCR method (Nucl. Acids Res., 16, 8186 (1988)).

As another method of obtaining the polynucleotide of the invention, there may be mentioned a method of preparation which is based on the amino acid sequence information concerning known polypeptides having the same function as in the present invention, namely glucose dehydrogenase activity. Thus, the highly conserved region is estimated by comparison between the amino acid sequences of the known polypeptides having glucose dehydrogenase activity.

Based on the amino acid sequences of the highly conserved regions, PCR (Polymerase Chain Reaction) primers for amplifying a part of the polynucleotide coding for the polypeptide of the invention are synthesized. A chromosomal DNA of that microorganism which is the origin of the polypeptide of the invention is prepared, the PCR is carried out using the above-mentioned PCR primers with this chromosomal DNA as the template to thereby amplify a part of the polynucleotide coding for said polypeptide, and the base sequence thereof is determined by proceeding in the same manner as mentioned above. Once this base sequence has been determined, the whole base sequence of the polynucleotide can be determined in the same manner as mentioned above, for example by the inverse PCR method.

As the thus-obtained DNA coding for the polypeptide of the invention, there may be mentioned, for example, a DNA having the base sequence shown in the sequence listing under SEQ ID NO:2, SEQ ID NO:4 or SEQ ID NO:12. In the following, an explanation is given of the base sequences respectively shown under SEQ ID NO:2, SEQ ID NO:4 and SEQ ID NO:12.

Re: DNA Sequence Coding for the Polypeptide of the Invention

As the DNA coding for the polypeptide of the invention, there may be mentioned, for example, a DNA having the base sequence shown in the sequence listing under SEQ ID NO:2, SEQ ID NO:4 or SEQ ID NO:12, or a DNA hybridizing with a DNA having a base sequence complementary to the base sequence shown in the sequence listing under SEQ ID NO:2, SEQ ID NO:4 or SEQ ID NO:12 under stringent conditions and coding for a polypeptide acting on glucose and NADP to form gluconolactone and NADPH.

The "DNA hybridizing with a DNA having a base sequence complementary to the base sequence shown in the sequence listing under SEQ ID NO:2 under stringent conditions and coding for a polypeptide acting on glucose and NADP to form gluconolactone and NADPH" so referred to herein means a DNA obtained by the use of the colony hybridization, plaque hybridization or southern hybridization technique, for instance, under stringent conditions using, as a probe, the DNA having a base sequence complementary to the base sequence shown in the sequence listing under SEQ ID NO:2, and coding for a polypeptide acting on glucose and NADP to form gluconolactone and NADPH.

The same shall apply also to the "DNA hybridizing with a DNA having a base sequence complementary to the base sequence shown in the sequence listing under SEQ ID NO:4 under stringent conditions and coding for a polypeptide acting on glucose and NADP to form gluconolactone and NADPH" and the "DNA hybridizing with a DNA having a base sequence complementary to the base sequence shown in the sequence listing under SEQ ID NO:12 under stringent conditions and coding for a polypeptide acting on glucose and NADP to form gluconolactone and NADPH".

The hybridization can be carried out according to the method described in Molecular Cloning, A laboratory manual, second edition (Cold Spring Harbor Laboratory Press, 1989), for instance. As the "DNA hybridizing under stringent conditions" so referred to herein, there may be mentioned, for example, a DNA obtainable by carrying out hybridization using a filter with a colony- or plaque-derived DNA immobilized thereon at 65° C. in the presence of 0.7-1.0 M NaCl and then washing the filter using a two-fold concentrated SSC solution (composition of 1-fold concentrated SSC solution: 150 mM sodium chloride and 15 mM sodium citrate) at 65° C., preferably with a 0.5-fold concentrated SSC solution at 65° C., more preferably with a 0.2-fold concentrated SSC solution at 65° C., and still more preferably with a 0.1-fold concentrated SSC solution at 65° C.

The hybridization conditions are not particularly restricted to those described above. It is possible for the one having ordinary skill in the art to properly select such a plurality of factors as temperature and salt concentration that are considered to influence the stringency of the hybridization and thus realize the optimum stringency.

As the DNA capable of hybridization under the conditions mentioned above, there may be mentioned a DNA having a sequence homology of not lower than 70%, preferably not lower than 80%, more preferably not lower than 90%, still more preferably not lower than 95%, most preferably not lower than 98%, with the DNA shown under SEQ ID NO:2, SEQ ID NO:4 or SEQ ID NO:12 and, so long as the polypeptide encoded can act on glucose and NADP to form gluconolactone and NADPH, it is included within the scope of the DNA mentioned above.

The "sequence homology (%)" so referred to herein is expressed in terms of the numerical value obtained by optimally aligning two DNAs to be compared, dividing the number of sites identical in nucleic acid base (e.g. A, T, C, G, U or I) in both the sequences by the total number of bases subjected to comparison and multiplying the resulting quotient by 100.

The following tools for sequence analysis, among others, can be used to calculate the sequence homology: GCG Wisconsin Package (Program Manual for The Wisconsin Package, Version 8, Sep., 1994, Genetics Computer Group, 575 Science Drive Medison, Wisconsin, USA 53711; Rice, P. (1996) Program Manual for EGCG Package, Peter Rice, The Sanger Centre, Hinxton Hall, Cambridge, CB10 1RQ, England), and the ExPASy World Wide Web molecular biology server (Geneva University Hospital and University of Geneva, Geneva, Switzerland).

Re: Host-Vector System and Transformant

A polypeptide expression vector can be constructed by inserting a DNA coding for the glucose dehydrogenase of the invention into an expression vector. By transforming a host organism with this recombinant vector and culturing the transformant obtained, it is possible to cause expression of the enzyme of the invention. Further, for example, the method which comprises introducing a polynucleotide coding for the enzyme of the invention into a chromosome can also be utilized.

The expression vector to be used in the above procedure is not particularly restricted so long as it allows the polypeptide encoded by the DNA to be expressed in an appropriate host organism. As such vector, there may be mentioned, for example, plasmid vectors, phage vectors, and cosmid vectors. Further, shuttle vectors capable of gene exchange between different host strains can also be used.

In the case of the host being *Escherichia coli*, such vector can suitably be used generally in the form of an expression vector comprising such a regulatory factor as the lacUV5 promoter, trp promoter, trc promoter, tac promoter, lpp promoter, tufB promoter, recA promoter or pL promoter and an expression unit operably linked to the DNA of the invention. For example, mention may be made of pUCN18 (cf. Example 3), pSTV28 (product of Takara Bio Inc.) and pUCNT (WO 94/03613).

The term "regulatory factor" as used herein refers to a base sequence comprising a functional promoter and an arbitrary related transcription element(s) (e.g. enhancer, CCAAT box, TATA box, SPI site, etc.).

The term "operably linked" as used herein refers to a condition in which various regulatory elements regulating the expression of the gene, such as a promoter and an enhancer, are linked to the gene so as to operate in host cells. It is well known to the one having ordinary skill in the art that the regulatory factor can vary in type and kind according to the host.

Those vectors, promoters and others which are utilizable in various organisms are described in detail in "Biseibutsugaku Kiso Koza 8: Idensikogaku (Basic Courses in Microbiology 8: Genetic Engineering), Kyoritsu Shuppan", for instance.

The host organism to be used for the expression of each polypeptide is not particularly restricted so long as it is capable of being transformed with a polypeptide expression vector containing the DNA coding for each polypeptide and allows the expression of the polypeptide encoded by the gene introduced. As utilizable organisms, there may be mentioned, for example, those bacteria for which host-vector systems have been developed, such as the genera *Escherichia, Bacillus, Pseudomonas, Serratia, Brevibacterium, Corynebacterium, Streptococcus,* and *Lactobacillus*; those actinomycetes for which host-vector systems have been developed, such as the genera *Rhodococcus* and *Streptomyces*; those yeasts for which host-vector systems have been developed, such as the genera *Saccharomyces, Kluyveromyces, Schizosaccharomyces, Zygosaccharomyces, Yarrowia, Trichosporon, Rhodosporidium, Pichia,* and *Candida*; and those fungi for which host-vector systems have been developed, such as the genera *Neurospora, Aspergillus, Cephalosporium,* and *Trichoderma.*

In addition to those in microorganisms, various host-vector systems have also been developed in plants and animals and, in particular, systems for large-scale foreign protein expression using such insects as silkworms (Nature 315, 592-594 (1985)) or such plants as rape, maize and potato have been developed; these, too, can suitably be utilized. Among those mentioned above, bacteria are preferred from the introduction and expression efficiency viewpoint, and *Escherichia coli* is particularly preferred.

The recombinant vector containing the DNA coding for the enzyme of the invention can be introduced into a host microorganism in the conventional manner. When, for example, the plasmid pNGLP (cf. Example 3), which is a vector of the invention resulting from introduction of the DNA shown under SEQ ID NO:2 into the above-mentioned expression vector pUCN18, is used as the recombinant vector and *Escherichia coli* as the host microorganism, a transformant, *E. coli* HB101(pNGLP) (cf. Example 5), resulting from introduction of that vector into cells of the host can be obtained by using commercially available *E. coli* HB101 competent cells (product of Takara Bio Inc.), for instance, and carrying out the procedure according to the protocol attached thereto.

When the plasmid pNGLP2 (cf. Example 4), which is a vector of the invention resulting from introduction of the DNA shown under SEQ ID NO:4 into the above-mentioned expression vector pUCN18, is used as the recombinant vector and *Escherichia coli* as the host microorganism, a transformant, *E. coli* HB101(pNGLP2) (cf. Example 5), resulting from introduction of that vector into cells of the host can be obtained by using commercially available *E. coli* HB101 competent cells (product of Takara Bio Inc.), for instance, and carrying out the procedure according to the protocol attached thereto.

Further, when the plasmid pNGPP2 (cf. Example 14), which is a vector of the invention resulting from introduction of the DNA shown under SEQ ID NO:12 into the above-mentioned expression vector pUCN18, is used as the recombinant vector and *Escherichia coli* as the host microorganism, a transformant, *E. coli* HB101(pNGPP2) (cf. Example 14), resulting from introduction of that vector into cells of the host can be obtained by using commercially available *E. coli* HB101 competent cells (product of Takara Bio Inc.), for instance, and carrying out the procedure according to the protocol attached thereto.

Also developable is a transformant in which two polypeptides, namely the glucose dehydrogenase of the invention and a polypeptide having reductase activity for which NADPH serves as a coenzyme, as mentioned later herein, both are expressed in one and the same cell. Thus, such a transformant can be obtained by inserting a DNA coding for the enzyme of the invention and a DNA coding for a polypeptide having reductase activity into one and the same vector and introducing the resultant vector into a host cell or, alternatively, by inserting these two DNAs respectively into two vectors belonging to different incompatibility groups and introducing them into one and the same host cell.

Production of NADPH from NADP and Glucose
[Reaction Conditions]

For the production of NADPH by conversion of NADP in the presence of glucose using the enzyme of the invention or a transformant in which the enzyme of the invention has been expressed, such a procedure as mentioned below may be followed, although the procedure to be employed is not limited thereto.

Glucose and NADP are added to an appropriate solvent such as 100 mM phosphate buffer (pH 7), for instance. To the solution is added the enzyme of the invention and/or the culture of a transformant containing the enzyme of the invention as expressed therein and/or a processed material derived therefrom or the like, and the reaction is allowed to proceed with stirring while the pH is adjusted.

The term "processed material" as used herein means a material retaining the catalytic activity of the enzyme of the invention such as, for example, a crude extract, cultured cells, lyophilized cells, acetone-dried cells, a cell disruption product, or a material carrying such a material in an immobilized form.

The reaction can be carried out either batchwise or in a continuous manner. Glucose is preferably added in an amount at least equimolar to NADP. NADP or glucose may be supplemented during the reaction.

This reaction is carried out at 5-80° C., preferably 10-60° C., more preferably 20-40° C., and the pH of the reaction mixture is maintained at 4-8.5, preferably 5-8, more preferably 6-7.5, particularly preferably 7.

In carrying out the reaction, an aqueous solvent may be used or, alternatively, a mixture of an aqueous solvent and an organic solvent may be used. As the organic solvent, there may be mentioned, for example, toluene, ethyl acetate, n-butyl acetate, hexane, isopropanol, diisopropyl ether, methanol, acetone and dimethyl sulfoxide.

Enzymatic Reduction Reaction Using a Reductase Source with NADPH as a Coenzyme
[Enzymatic Reduction Reaction]

When the enzymatic reduction reaction using a reductase source requiring NADPH as a coenzyme is carried out, NADPH as a coenzyme is required. The reaction can of course be carried out by adding a necessary amount of NADPH to the reaction system. However, by carrying out the reaction using the glucose dehydrogenase of the invention which is capable of converting the coenzyme in oxidized form (NADP) to the reduced form NADPH, together with glucose, it becomes possible to markedly reduce the amount of NADPH, which is expensive.

For efficiently regenerating NADPH in the enzymatic reduction reaction using a reductase source with NADPH as a coenzyme, the reaction may be carried out by adding the glucose dehydrogenase of the invention, glucose and NADP to the reduction reaction system but, when a transformant as transformed with both a DNA coding for the enzyme of the invention and a DNA coding for a reductase requiring NADPH as a coenzyme is used as the catalyst, the reaction can be carried out efficiently without the need of separately preparing a reductase requiring NADPH as a coenzyme and adding that reductase to the reaction system. Such transformant can be obtained by the method described hereinabove under "Re: Host-vector system and transformant".

[Reductase Requiring NADPH as a Coenzyme]

The source of the reductase requiring NADPH as a coenzyme is not particularly restricted so long as it shows reductase activity in the presence of NADPH as a coenzyme. Thus, for example, it may be one of various microorganisms, a processed material or purified enzyme derived therefrom, or a commercially available enzyme.

The term "processed material" as used herein means a material retaining the enzymatic catalytic activity of the polypeptide such as, for example, a crude extract, cultured cells, lyophilized cells, acetone-dried cells, a cell disruption product, or a material carrying such a material in an immobilized form. Further, the polypeptide itself or the relevant cells themselves can be used also in an immobilized form produced by any of those methods which are known in the art. The microorganism may also be a recombinant improved in reductase activity by gene recombination. The enzyme may be a known one or a newly found one.

As the enzyme showing reductase activity with NADPH as a coenzyme, there may be mentioned, for example, various reductases such as carbonyl reductases, aldehyde reductases, conjugated polyketone reductases and aldose reductases, various oxidoreductases such as alcohol dehydrogenases and malate dehydrogenases, and old yellow enzyme. In addition, mention may also be made of those reductases requiring NADPH as a coenzyme which are described in "Koso Handobukku (Enzyme Handbook)" (Asakura Publishing, 1982) or elsewhere.

[Reduction Reaction Conditions]

When the reduction reaction is carried out using a reductase source requiring NADPH as a coenzyme while NADP is converted to NADPH by the use of the enzyme of the invention or a transformant in which the enzyme of the invention has been expressed, the reaction can be carried out in the following manner. However, the method to be employed is not limited to the one described below.

Glucose, NADP and the carbonyl compound to be reduced are added to an appropriate solvent, for example 100 mM phosphate buffer (pH 7). Thereto are added the enzyme of the invention and/or the culture of a transformant in which the enzyme of the invention has been expressed and/or a processed material derived therefrom or the like, together with a reductase source requiring NADPH as a coenzyme, and the reaction is allowed to proceed with pH adjustment and stirring.

The term "processed material" as used herein means a material retaining the enzymatic catalytic activity of the polypeptide in question such as, for example, a crude extract, cultured cells, lyophilized cells, acetone-dried cells, a cell disruption product, or a material carrying such a material in an immobilized form.

The reaction can be carried out either batchwise or in a continuous manner. In the case of a batchwise run, the carbonyl compound, namely the substrate to be reduced, may be added at a concentration of 0.01 to 100% (w/v), preferably 0.1 to 70%, more preferably 0.5 to 50% based on the total reaction mixture. An additional amount of the substrate may be further added during the reaction.

This reaction is carried out at 5-80° C., preferably 10-60° C., more preferably 20-40° C., and the pH of the reaction mixture is maintained at 3-9, preferably 5-8, more preferably 5.5-7.5. The reaction may be carried out either batchwise or in a continuous manner.

In carrying out the reaction, an aqueous solvent may be used or a mixture of an aqueous solvent and an organic solvent may be used. As the organic solvent, there may be mentioned, for example, toluene, ethyl acetate, n-butyl acetate, hexane, isopropanol, diisopropyl ether, methanol, acetone and dimethyl sulfoxide.

Utilization in Biosensors

As the biosensor utilizing the enzyme of the invention or a transformant containing the enzyme of the invention as expressed therein, there may be mentioned, for example, biosensors for detecting the compounds listed below and/or determining the concentrations thereof.

(1) NADPH and/or NADP;
(2) D-Glucose or 2-Deoxy-D-Glucose.

A highly sensitive method of assaying glucose-6-phosphate and NADPH using an NADPH oxidase and a glucose-6-phosphate dehydrogenase (G-6-P dehydrogenase) is reported in a non-patent document, Hokkaido Industrial Research Institute Report, Vol. 293, pp. 141-145, 1994. NADPH and D-glucose or 2-deoxy-D-glucose can be assayed with high sensitivity by conducting experiments as described in the above-cited document using the glucose dehydrogenase of the invention in lieu of the glucose-6-phosphate dehydrogenase.

EXAMPLES

The following examples illustrate the present invention in detail. They are, however, by no means limitative of the scope of the invention. Detailed procedures and so forth concerning the recombinant DNA technology used in the following examples are described in the following monographs:

Molecular Cloning 2nd Edition (Cold Spring Harbor Laboratory Press, 1989), Current Protocols in Molecular Biology (Greene Publishing Associates and Wiley-Interscience).

Example 1

Isolation of DNA Coding for Polypeptide Having Glucose Dehydrogenase Activity of *Lactobacillus plantarum* JCM 1149 Strain A DNA coding for a polypeptide having glucose dehydrogenase activity was obtained from the *Lactobacillus plantarum* JCM 1149 strain in the following manner.
(PCR Primer Preparation)

Primer 1 (SEQ ID NO:5 in the sequence listing) and Primer 2 (SEQ ID NO:6 in the sequence listing) were designed and synthesized based on the highly conserved region amino acid sequence information obtained by comparison of the amino acid sequences of known glucose dehydrogenases, to amplify, by PCR, a part of the DNA coding for a polypeptide having glucose dehydrogenase activity.
(Cell Culture and Chromosomal DNA Preparation)

A commercially available liquid medium (pH 7), Difco Lactobacilli MRS Broth (product of Becton, Dickinson and Company), was distributed in 15-ml portions into large-size test tubes, followed by 20 minutes of steam sterilization at 120° C. Each of the liquid medium portions was inoculated aseptically with one loopful of the *Lactobacillus plantarum* JCM 1149 strain, and stationary culture was carried out at 30° C. for about 72 to 96 hours. Cells were collected by centrifugation. Chromosomal DNA preparation from the cells was made by using an UltraClean Microbiol DNA Isolation kit (product of MO BIO Laboratories) according to the protocol attached thereto.
(Gene Amplification by PCR)

PCR was carried out using the primers 1 and 2 prepared as mentioned above, with the chromosomal DNA obtained as the template, whereupon a DNA fragment, about 340 bp in length, which was considered to be a part of the desired gene, was amplified. The PCR was carried out using PrimeSTAR HS DNA Polymerase (product of Takara Bio Inc.) as the DNA polymerase under the reaction conditions recommended in the protocol attached thereto. The DNA fragment amplified was excised from the agarose gel and purified using QIAquick Gel Extraction Kit (product of Qiagen). The thus-purified amplified fragment was analyzed for the base sequence thereof by direct sequencing using BigDye Terminator Cycle Sequencing Kit (product of Applied Biosystems) and an Applied Biosystems 3130xl genetic analyzer (product of Applied Biosystems). Based on this base sequence information, the whole base sequence of the polynucleotide coding for the desired polypeptide was determined by the inverse PCR method mentioned below.
(Full-Length Sequence Determination of Desired Gene by Inverse PCR)

The *Lactobacillus plantarum* JCM 1149 strain-derived chromosomal DNA prepared as described above was fully digested with the restriction enzyme HindIII or SacI, and each polynucleotide fragment mixture obtained was subjected to intramolecular cyclization using T4 ligase. The whole base sequence, including the base sequence determined as described above, of the gene was determined by the inverse PCR method (Nucl. Acids Res., 16, 8186 (1988)) using the cyclization product as the template. The result is shown in the sequence listing under SEQ ID NO:2. The inverse PCR was carried out using TAKARA LA Taq (product of Takara Bio Inc.) as the DNA polymerase under the reaction conditions recommended in the protocol attached thereto. The amino acid sequence of the polypeptide (hereinafter abbreviated as "GLP") encoded by the base sequence shown under SEQ ID NO:2 is shown under SEQ ID NO:1.

Example 2

Isolation of DNA Coding for Polypeptide Having Glucose Dehydrogenase Activity of *Lactobacillus pentosus* JCM 1558 Strain A chromosomal DNA of the *Lactobacillus pentosus* JCM 1558 strain was prepared in the same manner as mentioned above in Example 1. Then, PCR was carried out using the primers 1 and 2 prepared in Example 1, with the chromosomal DNA prepared as the template, whereupon a polynucleotide fragment, about 340 bp in length, presumably a part of the desired gene, was amplified. The base sequence of the amplified polynucleotide fragment was analyzed and determined in the same manner as in Example 1. Based on this base sequence information, the whole base sequence of the polynucleotide coding for the desired polypeptide was determined by the inverse PCR method mentioned below.

The *Lactobacillus pentosus* JCM 1558 strain-derived chromosomal DNA prepared as described above was fully digested with the restriction enzyme SpeI or EcoRI, and each polynucleotide fragment mixture obtained was subjected to intramolecular cyclization using T4 ligase. The whole base sequence, including the base sequence determined as described above, of the gene was determined by the inverse PCR method in the same manner as in Example 1, using the cyclization product as the template. The result is shown in the sequence listing under SEQ ID NO:4. The amino acid sequence of the polypeptide (hereinafter abbreviated as "GLP2") encoded by the base sequence shown under SEQ ID NO:4 is shown under SEQ ID NO:3.

Example 3

Construction of Recombinant Vector pNGLP

PCR was carried out using Primer 3 (SEQ ID NO:7 in the sequence listing) and Primer 4 (SEQ ID NO:8 in the sequence listing), with the *Lactobacillus plantarum* JCM 1149 strain-derived chromosomal DNA as the template. As a result, there was obtained a double-stranded polynucleotide resulting from addition of an NdeI recognition site to the initiation codon site of the gene having the base sequence shown in the sequence listing under SEQ ID NO:2 and further addition, just behind the termination codon, of a new termination codon (TAA) and an SphI recognition site. The PCR was carried out using Pyrobest DNA Polymerase (product of Takara Bio Inc.) as the DNA polymerase under the reaction conditions recommended in the protocol attached thereto.

The polynucleotide fragment obtained by the above-mentioned PCR was partially digested with NdeI and SphI, and the digestion product was inserted into the plasmid pUCN18 (plasmid derived from pUC18 (product of Takara Bio Inc.; GenBank Accession No. L09136) by converting the 185th base T to A by PCR for destruction of the NdeI site and further converting the 471st-472nd bases GC to TG for introduction of a new NdeI site) at a site between the NdeI recognition site and SphI recognition site downstream from the lac promoter; a recombinant vector, pNGLP, was thus constructed.

Example 4

Construction of Recombinant Vector pNGLP2

PCR was carried out using Primer 5 (SEQ ID NO:9 in the sequence listing) and Primer 6 (SEQ ID NO:10 in the sequence listing), with the *Lactobacillus pentosus* JCM 1558 strain-derived chromosomal DNA as the template. As a result, there was obtained a double-stranded polynucleotide resulting from addition of an NdeI recognition site to the initiation codon site of the gene having the base sequence shown in the sequence listing under SEQ ID NO:4 and further addition, just behind the termination codon, of a new termination codon (TAA) and a PstI recognition site. The PCR was carried out using Pyrobest DNA Polymerase (product of Takara Bio Inc.) as the DNA polymerase under the reaction conditions recommended in the protocol attached thereto.

The polynucleotide fragment obtained by the above-mentioned PCR was digested with NdeI and PstI, and the digestion product was inserted into the plasmid pUCN18 at a site between the NdeI recognition site and PstI recognition site downstream from the lac promoter; a recombinant vector, pNGLP2, was thus constructed.

Example 5

Transformant Production

*E. coli* HB101 competent cells (product of Takara Bio Inc.) were transformed with the recombinant vector pNGLP constructed in Example 3 and the recombinant vector pNGLP2 constructed in Example 4, respectively, according to the protocol attached to the *E. coli* HB101 competent cells; the transformant *E. coli* HB101(pNGLP) or *E. coli* HB101(pNGLP2) was obtained.

Example 6

Polypeptide Expression in Transformants

The two transformants obtained in Example 5 and *E. coli* HB101(pUCN18) (Comparative Example), a transformant harboring the vector plasmid pUCN18, were respectively inoculated into 5-ml portions of 2×YT medium (tryptone 1.6%, yeast extract 1.0%, NaCl 0.5%, pH 7.0) containing 200 μg/ml of ampicillin and shake-cultured at 37° C. for 24 hours. Cells were collected from each culture by centrifugation and then suspended in 5 ml of 100 mM phosphate buffer (pH 6.5). The cells were disrupted using a model UH-50 ultrasonic homogenizer (product of SMT) and the cell debris was then removed by centrifugation to give a cell-free extract. Each cell-free extract was assayed for glucose dehydrogenase activity.

Glucose (100 mM), NADP (2 mM) and the crude enzyme solution were added to 1.0 M Tris-hydrochloride buffer (pH 8.0) and the reaction was allowed to proceed at 25° C., and the glucose dehydrogenase activity was calculated from the rate of increase in absorbance at the wavelength 340 nm. The enzyme activity causing reduction of 1 μmol (micromole) of NADP to NADPH in 1 minute under these conditions was defined as 1 U.

In E. coli HB101(pNGLP) or E. coli HB101(pNGLP2), increases in absorbance were observed in the activity measurement system, hence the production of NADPH from NADP and glucose could be confirmed. In E. coli HB101 (pUCN18) (comparative control), no increases in absorbance were found in the activity measurement system, hence the production of NADPH could not be observed.

The glucose dehydrogenase activities of the respective transformants were as summarized in Table 1 in terms of specific activity. As shown in Table 1, the two transformants obtained in Example 5 each showed glucose dehydrogenase activity.

TABLE 1

| | Specific activity (U/mg) |
|---|---|
| E. coli HB101 (pNGLP) | 470 |
| E. coli HB101 (pNGLP2) | 95 |
| E. coli HB101 (pUCN18) | <0.01 |

From the above results, it could be confirmed that the polypeptides encoded by the DNAs obtained in Example 1 and Example 2, respectively, are enzymes capable of forming NADPH from NADP and glucose, namely glucose dehydrogenases.

Example 7

NADP/NAD Activity Ratio Measurement of GLP and GLP2

Using the cell-free extracts obtained in Example 6 from the transformants in which GLP and GLP2, respectively, had been expressed, activity measurements were made using NADP or NAD as a coenzyme. In the case of NADP, glucose dehydrogenase activities were measured by the method described in Example 6. In the case of NAD, the activity measurements were carried out in the same manner as in Example 6 except that NAD was used in lieu of NADP in the glucose dehydrogenase activity measurement method described therein. In comparative examples, the activities of three commercially available reagent enzymes, namely Bacillus megaterium-derived glucose dehydrogenase (product of Sigma), Bacillus sp.-derived glucose dehydrogenase (product of Wako) and Cryptococcus uniguttulatus-derived NADP-specific glucose dehydrogenase (product of Sigma), were measured in the same manner using NADP or NAD as a coenzyme. In a further comparative example, a transformant for the expression of Cryptococcus uniguttulatus JCM 3687 strain-derived NADP-specific glucose dehydrogenase was produced and grown by the method described in Japanese Kokai Publication 2006-262767, and the cell-free extract derived therefrom was also subjected to activity measurements in the same manner as mentioned above using NADP and NAD as coenzymes, respectively.

The relative activities, with the activity value obtained by using NADP as the coenzyme being taken as 100%, and the NADP/NAD activity ratios were as summarized in Table 2.

TABLE 2

| | | Relative activity (%) | | NADP/NAD activity ratio |
|---|---|---|---|---|
| | Origin | NADP | NAD | |
| GLP | Lactobacillus plantarum JCM1149 | 100 | 0.0093 | 10763 |
| GLP2 | Lactobacillus pentosus JCM1558 | 100 | 0.0098 | 10230 |
| Glucose dehydrogenase (Sigma) | Bacillus megaterium | 100 | 435 | 0.23 |
| Glucose dehydrogenase (Wako) | Bacillus sp. | 100 | 94 | 1.06 |
| NADP specific glucose dehydrogenase (Sigma) | Cryptococus uniguttulatus | 100 | 1.49 | 67.1 |
| NADP specific glucose dehydrogenase (JP2006-262767) | Cryptococus uniguttulatus JCM3687 | 100 | 1.58 | 63.1 |

The glucose dehydrogenases of the invention were both very high in NADP/NAD activity ratio and the values thereof were higher than 10,000. The NADP/NAD activity ratio values shown by them were more than 100 times higher as compared with the comparative examples, namely the commercial NADP-specific glucose dehydrogenase and the NADP-specific glucose dehydrogenase described in Japanese Kokai Publication 2006-262767. Thus, the glucose dehydrogenases of the present invention showed much higher levels of NADP specificity than the NADP-specific glucose dehydrogenases known in the art.

Example 8

Substrate Specificities of GLP and GLP2

Using the cell-free extracts obtained in Example 6 from the transformants in which GLP and GLP2, respectively, had been expressed, their activities with various monosaccharides other than glucose were measured. The activity measurements were carried out in the same manner as in Example 6 except that each monosaccharide to be evaluated was added in lieu of glucose in the activity measurement method described therein.

The relative activities, with the activity value obtained by using glucose as the substrate being taken as 100%, were as summarized in Table 3.

TABLE 3

| | Relative activity (%) | |
|---|---|---|
| | GDHLP | GDHLP2 |
| D-glucose | 100 | 100 |
| D-mannose | 6.8 | 5.7 |
| D-galactose | 4.2 | 3.5 |

TABLE 3-continued

|  | Relative activity (%) | |
| --- | --- | --- |
|  | GDHLP | GDHLP2 |
| D-fructose | <0.1 | <0.1 |
| D-glucose-6-phosphoric acid | 3.0 | 2.2 |
| 2-Deoxy-D-glucose | 108 | 113 |
| D-glucosamine | 8.5 | 7.3 |
| N-acetyl-D-glucosamine | <0.1 | <0.1 |
| D-ribose | <0.1 | <0.1 |
| D-xylose | 3.3 | 2.8 |
| D-arabinose | <0.1 | <0.1 |

GLP and GLP2 both showed high levels of activity with D-glucose and 2-deoxy-D-glucose. Since their activity levels with D-glucose-6-phosphate are very low as compared with the activity levels with D-glucose, both GLP and GLP2 can be said to be glucose dehydrogenases, not glucose-6-phosphate dehydrogenases.

Example 9

Optimum Reaction pH Levels for GLP and GLP2

Using cell-free extracts obtained from the transformants in which GLP and GLP2, respectively, had been expressed as in Example 6, the optimum reaction pH levels therefor were determined. The activity measurements were carried out in the same manner as in Example 6 except that 0.1 M Britton-Robinson buffers (pH 4 to 9) were used in lieu of 1.0 M Tris-hydrochloride buffer (pH 8.0) in the activity measurement method described therein.

The relative activities, with the activity value obtained at pH 7 being taken as 100%, were as summarized in Table 4.

TABLE 4

|  | Relative activity (%) | |
| --- | --- | --- |
| pH | GLP | GLP2 |
| 4.0 | 21 | 26 |
| 4.5 | 45 | 39 |
| 5.0 | 61 | 46 |
| 5.5 | 70 | 51 |
| 6.0 | 82 | 65 |
| 6.5 | 95 | 85 |
| 7.0 | 100 | 100 |
| 7.5 | 86 | 68 |
| 8.0 | 46 | 18 |
| 8.5 | 13 | 2.4 |
| 9.0 | 2.1 | 0.2 |

For both GLP and GLP2, the optimum pH was around 7.

Example 10

Synthesis of ethyl (S)-4-chloro-3-hydroxybutyrate using GLP

E. coli HB101(pNTS1), a recombinant *Escherichia coli* strain, was produced by the method described in International Publication WO 98/35025. This bacterial strain was inoculated into 5 ml of 2×YT medium (tryptone 1.6%, yeast extract 1.0%, NaCl 0.5%, pH 7.0) containing 200 µg/ml of ampicillin and shake-cultured at 37° C. for 24 hours. Cells were collected by centrifugation and then suspended in 5 ml of 100 mM phosphate buffer (pH 6.5). The cells were disrupted using a model UH-50 ultrasonic homogenizer (product of SMT) and the cell debris was then removed by centrifugation to give a cell-free extract. This extract was assayed for CRD activity by the method described in the above-cited publication and was found active; the specific activity was 15 U/mg.

To 45 ml of the cell-free extract prepared from E. coli HB101(pNTS1) by the method described above were added 5 ml of the cell-free extract of E. coli HB101(pNGLP) as prepared by the method described in Example 6, 5.5 g of glucose and 1.6 mg of NADP and, while the mixture was adjusted to pH 6.5 with a 5 M aqueous solution of sodium hydroxide and stirred at 30° C., ethyl 4-chloroacetoacetate was added in 250-mg portions at 15-minute intervals. The reaction was allowed to proceed for a total of 5 hours while adding a total amount of 5 g of ethyl 4-chloroacetoacetate in that manner. Thereafter, the reaction mixture was extracted with ethyl acetate, the solvent was then removed, and the remaining extract was analyzed by gas chromatography under the conditions given below, whereupon the formation of ethyl 4-chloro-3-hydroxybutyrate in 95% yield was revealed. The product ethyl 4-chloro-3-hydroxybutyrate was analyzed for optical purity by high-performance liquid chromatography under the conditions given below; it was found to be in the S form with 100% e.e.

Thus, it could be confirmed that when an enzymatic reduction reaction using a reductase, CRD in this example, with NADPH as a coenzyme is carried out while NADPH is regenerated using the glucose dehydrogenase GLP of the invention, the reduction reaction proceeds very efficiently.

[Gas Chromatography Conditions]

Using a glass column (ID 3 mm×1 m) packed with PEG-20M Chromosorb WAW DMCS 10% 80/100 mesh (product of GL Sciences), the chromatography was carried out at 150° C. using an FID for detection.

[High-Performance Liquid Chromatography Conditions]

The optical resolution column CHIRALCEL OB (product of Daicel Chemical Industries) was used. Using a mixed solvent having the composition of n-hexane/isopropanol=9/1 as the mobile phase, the chromatography was carried out at a mobile phase flow rate of 0.8 ml/minute. Absorbance measurements were made at 215 nm for detection.

Example 11

Synthesis of ethyl (S)-4-chloro-3-hydroxybutyrate using GLP2

The reaction procedure of Example 10 was followed in the same manner except that the cell-free extract of E. coli HB101(pNGLP2) as prepared by the method described in Example 6 was used in lieu of the cell-free extract of E. coli HB101(pNGLP). After the reaction, the reaction mixture was extracted with ethyl acetate and the solvent was then removed to give ethyl (S)-4-chloro-3-hydroxybutyrate with 100% e.e. in 94% yield.

Thus, it could be confirmed that when an enzymatic reduction reaction using a reductase, CRD in this example, with NADPH as a coenzyme is carried out while NADPH is regenerated using the glucose dehydrogenase GLP2 of the invention, the reduction reaction proceeds very efficiently.

Comparative Example 1

Synthesis of ethyl (S)-4-chloro-3-hydroxybutyrate without addition of either of GLP and GLP2

The reaction procedure of Example 10 was followed in the same manner except that the cell-free extract of *E. coli* HB101(pUCN18) as prepared by the method described in Example 6 and found to have no glucose dehydrogenase activity was used in lieu of the cell-free extract of *E. coli* HB101(pNGLP). After the reaction, the reaction mixture was extracted with ethyl acetate and the solvent was then removed; almost no ethyl 4-chloro-3-hydroxybutyrate was obtained.

The utility of the use of the glucose dehydrogenase of the invention in enzymatic reduction reactions could be confirmed also from the result of this comparative example.

Example 12

Isolation of DNA Coding for Polypeptide Having Glucose Dehydrogenase Activity of *Pediococcus parvulus* JCM 5889 Strain PCR was carried out using Primer 7 (SEQ ID NO:13 in the sequence listing) and Primer 8 (SEQ ID NO:14 in the sequence listing), with the *Pediococcus parvulus* JCM 5889 strain-derived chromosomal DNA as the template. As a result, there was obtained a double-stranded polynucleotide resulting from addition of an NdeI recognition site to the initiation codon site of the gene and further addition, just behind the termination codon, of a new termination codon (TAA) and a SalI recognition site. The PCR was carried out using PrimeSTAR HS DNA Polymerase (product of Takara Bio Inc.) as the DNA polymerase under the reaction conditions recommended in the protocol attached thereto. Further, the base sequence of the polynucleotide was analyzed using BigDye Terminator Cycle Sequencing Kit (product of Applied Biosystems) and an Applied Biosystems 3130xl genetic analyzer (product of Applied Biosystems). The result is shown in the sequence listing under SEQ ID NO:12. The amino acid sequence of the polypeptide (hereinafter referred to as "GPP2") encoded by that polynucleotide is shown under SEQ ID NO:11.

Example 13

Construction of Recombinant Vector pNGPP2

The polynucleotide fragment obtained in Example 12 was digested with NdeI and SalI, and the digestion product was inserted into the plasmid pUCN18 (plasmid derived from pUC18 (product of Takara Bio Inc.; GenBank Accession No. L09136) by converting the 185th base T to A by PCR for destruction of the NdeI site and further converting the 471st-472nd bases GC to TG for introduction of a new NdeI site) at a site between the NdeI recognition site and SalI recognition site downstream from the lac promoter; a recombinant vector, pNGPP2, was thus constructed.

Example 14

Transformant Production

*E. coli* HB101 competent cells (product of Takara Bio Inc.) were transformed with the recombinant vector pNGPP2 constructed in Example 13 according to the protocol attached to the *E. coli* HB101 competent cells; a transformant, *E. coli* HB101(pNGPP2), was thus obtained.

Example 15

Polypeptide Expression in Transformants

The transformant *E. coli* HB101(pNGPP2) obtained in Example 14 and *E. coli* HB101(pUCN18) (Comparative Example), a transformant harboring the vector plasmid pUCN18, were respectively inoculated into 5-ml portions of 2×YT medium (tryptone 1.6%, yeast extract 1.0%, NaCl 0.5%, pH 7.0) containing 200 µg/ml of ampicillin, followed by 24 hours of shake culture at 37° C. Cells were collected from each culture by centrifugation and then suspended in 5 ml of 100 mM phosphate buffer (pH 6.5). The cells were disrupted using a model UH-50 ultrasonic homogenizer (product of SMT) and the cell debris was then removed by centrifugation to give a cell-free extract. Each cell-free extract was assayed for glucose dehydrogenase activity.

Glucose (100 mM), NADP (2 mM) and the crude enzyme solution were added to 1.0 M Tris-hydrochloride buffer (pH 8.0) and the reaction was allowed to proceed at 25° C., and the glucose dehydrogenase activity was calculated from the rate of increase in absorbance at the wavelength 340 nm. The enzyme activity causing reduction of 1 µmol (micromole) of NADP to NADPH in 1 minute under these conditions was defined as 1 U.

In *E. coli* HB101(pNGPP2), increases in absorbance were observed in the activity measurement system, hence the production of NADPH from NADP and glucose could be confirmed. In *E. coli* HB101(pUCN18) (comparative control), no increases in absorbance were found in the activity measurement system, hence the production of NADPH could not be observed.

The glucose dehydrogenase activities of the respective transformants were as summarized in Table 5 in terms of specific activity. As shown in Table 5, the transformant obtained in Example 14 showed glucose dehydrogenase activity.

TABLE 5

|  | Specific activity (U/mg) |
| --- | --- |
| *E. coli* HB101(pNGPP2) | 62 |
| *E. coli* HB101(pUCN18) | <0.01 |

The polypeptide (GPP2) encoded by the DNA having the base sequence shown in the sequence listing under SEQ ID NO:12 and having the amino acid sequence shown in the sequence listing under SEQ ID NO:11 had glucose dehydrogenase activity.

Example 16

NADP/NAD Activity Ratio Measurement of GPP2

The cell-free extract obtained in Example 15 from the transformant after expression of GPP2 was subjected to NADP/NAD activity ratio measurement in the same manner as in Example 7. The relative activity, with the activity value obtained by using NADP as the coenzyme being taken as 100%, and the NADP/NAD activity ratio were as summarized in Table 6.

TABLE 6

| | Origin | Relative activity (%) | | NADP/NAD activity ratio |
| --- | --- | --- | --- | --- |
| | | NADP | NAD | |
| GPP2 | Pediococcus parvulus JCM5889 | 100 | 0.0097 | 10284 |
| Glucose dehydrogenase (Sigma) | Bacillus megaterium | 100 | 435 | 0.23 |
| Glucose dehydrogenase (Wako) | Bacillus sp. | 100 | 94 | 1.06 |
| NADP specific glucose dehydrogenase (Sigma) | Cyptococus uniguttulatus | 100 | 1.49 | 67.1 |
| NADP specific glucose dehydrogenase (JP2006-262767) | Cyptococus uniguttulatus JCM3687 | 100 | 1.58 | 63.1 |

The glucose dehydrogenase GPP2 of the invention was very high in NADP/NAD activity ratio and the value thereof was higher than 10,000. The NADP/NAD activity ratio value shown thereby was more than 100 times higher as compared with the comparative examples, namely the commercial NADP-specific glucose dehydrogenase and the NADP-specific glucose dehydrogenase described in Japanese Kokai Publication 2006-262767. Thus, the glucose dehydrogenase of the present invention had a much higher level of NADP specificity than the NADP-specific glucose dehydrogenases known in the art.

Example 17

Substrate Specificity of GPP2

Using the cell-free extract obtained in Example 15 from the transformant in which GPP2 had been expressed, its activities with various monosaccharides other than glucose were measured in the same manner as in Example 8. The relative activity values, with the activity value obtained by using glucose as the substrate being taken as 100%, were as summarized in Table 7.

TABLE 7

| | Relative activity (%) |
| --- | --- |
| D-glucose | 100 |
| D-mannose | 12 |
| D-galactose | 7.1 |
| D-fructose | <0.1 |
| D-glucose-6-phosphoric acid | 5.2 |
| 2-Deoxy-D-glucose | 99 |
| D-glucosamine | 15 |
| N-acetyl-D-glucosamine | <0.1 |
| D-ribose | 0.17 |
| D-xylose | 5.8 |
| D-arabinose | <0.1 |

GPP2 showed high levels of activity with D-glucose and 2-deoxy-D-glucose. Since the activity level with D-glucose-6-phosphate is very low as compared with the activity level with D-glucose, GPP2 can be said to be a glucose dehydrogenase, not a glucose-6-phosphate dehydrogenase.

Example 18

Optimum Reaction pH Level for GPP2

Using a cell-free extract obtained from the transformant in which GPP2 had been expressed as in Example 15, the optimum reaction pH level therefor was determined in the same manner as in Example 9. The relative activities, with the activity value obtained at pH 7 being taken as 100%, were as summarized in Table 8.

TABLE 8

| pH | Relative activity (%) |
| --- | --- |
| 4.0 | 51 |
| 5.0 | 60 |
| 6.0 | 67 |
| 6.5 | 81 |
| 7.0 | 100 |
| 7.5 | 98 |
| 8.0 | 54 |
| 8.5 | 14 |
| 9.0 | 2.0 |

The optimum pH for GPP2 was around 7.

Example 19

Synthesis of (R)-3-chloro-1,2-propanediol using GPP2

(R)-3-Chloro-1,2-propanediol was synthesized from racemic 3-chloro-1,2-propanediol according to the method described in International Publication WO 2006/090814. In the experiment, the recombinant microorganisms specified below were used; these have been deposited with the International Patent Organism Depositary (IPOD), National Institute of Advanced Industrial Science and Technology (Central 6, Higashi 1-1, Tsukuba City, 305-8566 Ibaraki Prefecture, Japan).

E. coli HB101(pTSCS) FERM BP-10024: a recombinant Escherichia coli strain as transformed with the Cellulomonas sp. KNK 0102 strain-derived glycerol dehydrogenase gene (cf. International Publication WO 05/123921).

E. coli HB101(pNTS1) FERM BP-5834: a recombinant Escherichia coli strain as transformed with the Candida magnoliae IFO 0705 strain-derived NADP-dependent reductase gene (cf. International Publication WO 98/035025).

E. coli HB101(pTSCS) FERM BP-10024 was inoculated into 50 ml of sterilized 2×YT medium (tryptone 1.6%, yeast extract 1.0%, NaCl 0.5%, pH 7.0) containing 200 μg/ml of ampicillin and shake-cultured at 37° C. for 18 hours. Cells were collected by centrifugation and then suspended in 50 ml of 100 mM phosphate buffer (pH 7.0).

Further, E. coli HB101(pNTS1) FERM BP-5834 was inoculated into 50 ml of 2×YT medium (tryptone 1.6%, yeast extract 1.0%, NaCl 0.5%, pH 7.0) containing 200 μg/ml of ampicillin and shake-cultured at 37° C. for 18 hours. Cells were collected by centrifugation and then suspended in 50 ml of 100 mM phosphate buffer (pH 7). The cells were disrupted using a model UH-50 ultrasonic homogenizer (product of SMT) to give a cell-free extract.

To a flask were added 2 ml of the *E. coli* HB101(pTSCS) suspension mentioned above, 40 mg of racemic 3-chloro-1,2-propanediol, 0.2 ml of the *E. coli* HB101(pNTS1)-derived cell-free extract mentioned above, 0.3 mg of NADP and 100 mg of glucose. Thereto was added the *E. coli* HB101 (pNGPP2)-derived cell-free extract (glucose dehydrogenase activity: 10 U) prepared by the method described in Example 15, and the reaction was allowed to proceed with stirring at 30° C. for 24 hours, while the mixture was adjusted to pH 7 with a 1 M aqueous solution of sodium hydroxide. Thereafter, ammonium sulfate was added to the reaction mixture until saturation, followed by extraction with ethyl acetate. The 3-chloro-1,2-propanediol content in the extract was determined by gas chromatography under the conditions (1) given below, and the yield was calculated. The optical purity of the 3-chloro-1,2-propanediol was analyzed by trifluoroacetylation and the subsequent gas chromatography under the conditions (2) given below. As a result, (R)-3-chloro-1,2-propanediol was obtained in 94% yield and the optical purity thereof was 98.7% e.e.

Thus, it could be confirmed that when, in such enzymatic reduction reaction using a reductase requiring NADPH as a coenzyme, NADPH is regenerated by using the glucose dehydrogenase GPP2 of the invention, the reduction reaction proceeds very efficiently.

[Gas Chromatography Conditions (1)]
Column: HP-5 (30 m×0.32 mm I.D.) (product of Agilent Technologies)
Detection: FID
Column temperature: Initial temperature 50° C., Final temperature 200° C., Programming rate 6° C./minute
Injection temperature: 150° C.
Detection temperature: 300° C.

[Gas Chromatography Conditions (2)]
Column: Chiradex G-PN (30 m×0.32 mm I.D.) (product of ASTEC)
Detection: FID
Column temperature: 90° C.
Injection temperature: 150° C.
Detection temperature: 150° C.
Detection time: R-form 10.0 min.; S-form 10.6 min.

Example 20

Synthesis of ethyl (S)-4-chloro-3-hydroxybutyrate

*E. coli* HB101(pNTS1) FERM BP-5834 was inoculated into 5 ml of 2×YT medium (tryptone 1.6%, yeast extract 1.0%, NaCl 0.5%, pH 7.0) containing 200 μg/ml of ampicillin and shake-cultured at 37° C. for 24 hours. Cells were collected by centrifugation and then suspended in 5 ml of 100 mM phosphate buffer (pH 6.5). The cells were disrupted using a model UH-50 ultrasonic homogenizer (product of SMT) and the cell debris was then removed by centrifugation to give a cell-free extract.

To 45 ml of the cell-free extract prepared from *E. coli* HB101(pNTS1) by the method described above were added 5 ml of the cell-free extract of *E. coli* HB101(pNGPP2) as prepared by the method described in Example 4, 5.5 g of glucose and 1.6 mg of NADP and, while the mixture was adjusted to pH 6.5 with a 5 M aqueous solution of sodium hydroxide and stirred at 30° C., ethyl 4-chloroacetoacetate was added in 250-mg portions at 15-minute intervals. The reaction was allowed to proceed for a total of 5 hours while adding a total amount of 5 g of ethyl 4-chloroacetoacetate in that manner. Thereafter, the reaction mixture was extracted with ethyl acetate, the solvent was then removed, and the remaining extract was analyzed by gas chromatography under the conditions given below, whereupon the formation of ethyl 4-chloro-3-hydroxybutyrate in 96% yield was revealed. The product ethyl 4-chloro-3-hydroxybutyrate was analyzed for optical purity by high-performance liquid chromatography under the conditions given below; it was found to be in the S form with 100% e.e.

Thus, it could be confirmed that when, in such enzymatic reduction reaction using a reductase requiring NADPH as a coenzyme, NADPH is regenerated by using the glucose dehydrogenase GPP2 of the invention, the reduction reaction proceeds very efficiently to give the haloalcohol ethyl (S)-4-chloro-3-hydroxybutyrate.

[Gas Chromatography Conditions]
Using a glass column (ID 3 mm×1 m) packed with PEG-20M Chromosorb WAW DMCS 10% 80/100 mesh (product of GL Sciences), the chromatography was carried out at 150° C. using an FID for detection.

[High-Performance Liquid Chromatography Conditions]
The optical resolution column CHIRALCEL OB (product of Daicel Chemical Industries) was used. Using a mixed solvent having the composition of n-hexane/isopropanol=9/1 as the mobile phase, the chromatography was carried out at a mobile phase flow rate of 0.8 ml/minute. For detection, absorbance measurements were made at 215 nm.

The invention claimed is:

1. A recombinant vector comprising a DNA coding for a NADP-specific glucose dehydrogenase showing a NADP/NAD activity ratio of no lower than 300, derived from *Lactobacillus plantarum*, which is selected from the group consisting of:
   (a) a DNA comprising SEQ ID NO: 2;
   (b) a DNA coding for a polypeptide having the amino acid sequence of SEQ ID NO: 1; and
   (c) a DNA coding for a polypeptide at least 90% sequence identical to the polypeptide of SEQ ID NO: 1.

2. A transformant obtained by transforming a host cell with the vector of claim 1.

3. A reduction reaction system for an enzymatic reduction reaction using a reductase source requiring NADPH as a coenzyme, wherein the reduction reaction system comprises the transformant of claim 2.

4. The reduction reaction system according to claim 3, wherein the transformant further comprises a DNA coding for a reductase requiring NADPH as a coenzyme.

5. A biosensor comprising the transformant of claim 2.

6. A method for detecting NADPH and/or NADP and/or measuring the concentration of NADPH and/or NADP in a sample which comprises contacting the sample with the biosensor of claim 5.

7. A method for detecting D-glucose or 2-deoxy-D-glucose and/or measuring the concentration of D-glucose or 2-deoxy-D-glucose in a sample which comprises contacting the sample with the biosensor of claim 5.

* * * * *

SEQUENCE LISTING

```
<160> NUMBER OF SEQ ID NOS: 14

<210> SEQ ID NO 1
<211> LENGTH: 261
<212> TYPE: PRT
<213> ORGANISM: Lactobacillus plantarum

<400> SEQUENCE: 1

Met Tyr Glu Asp Leu Asn Gly Lys Val Ala Val Ile Thr Gly Gly Ser
1               5                   10                  15

Lys Gly Ile Gly Ser Ala Ile Ala Lys Arg Phe Gly Glu Glu Lys Met
            20                  25                  30

Lys Val Val Ile Asn Tyr Asn Ser Asp Pro Ala Gly Ala Gln Lys Ala
        35                  40                  45
```

```
Ala Asp Thr Val Lys Val Ala Gly Gly Asp Ala Val Ile Val Gln Ala
 50                  55                  60
Asn Ile Ala Ser Glu Ala Gly Val Asp Ala Leu Leu Ala Ala Ala Ile
 65                  70                  75                  80
Asp His Phe Gly Asp Leu Asp Val Trp Val Asn Asn Ala Gly Met Glu
                 85                  90                  95
Ile Lys Ser Pro Thr His Glu Val Ser Leu Asp Asp Trp Asn Lys Val
                100                 105                 110
Thr Ala Ile Asp Gln Thr Gly Val Phe Leu Gly Ser Arg Thr Ala Leu
            115                 120                 125
Ala Tyr Phe Lys Ala His Gln Lys Pro Gly Asn Ile Ile Asn Met Ser
130                 135                 140
Ser Val His Glu Arg Ile Pro Trp Pro Thr Phe Ala Ser Tyr Ala Ala
145                 150                 155                 160
Ala Lys Gly Ser Val Lys Leu Phe Thr Gln Thr Ile Ala Met Glu Tyr
                165                 170                 175
Ala Gln Asp Asn Ile Arg Val Asn Ala Ile Gly Pro Gly Ala Ile Asn
            180                 185                 190
Thr Pro Ile Asn Ala Glu Lys Phe Ala Asp Pro Gln Gln Tyr Asp Gln
        195                 200                 205
Thr Val Asn Met Val Pro Met Asn Arg Ile Gly Thr Pro Glu Glu Val
210                 215                 220
Ala Ala Gly Ala Ala Trp Leu Ala Ser Ser Glu Ser Ser Tyr Val Thr
225                 230                 235                 240
Gly Ile Thr Leu Phe Ile Asp Gly Gly Met Thr Leu Tyr Pro Ala Phe
                245                 250                 255
Lys Asp Gly Gln Gly
            260

<210> SEQ ID NO 2
<211> LENGTH: 786
<212> TYPE: DNA
<213> ORGANISM: Lactobacillus plantarum

<400> SEQUENCE: 2
atgtatgaag atttaaatgg taaggtagca gtcattacag gtggctctaa aggaattggt     60
tcggcaatcg ccaaaagatt tggtgaagaa aaaatgaaag tggtcattaa ctataatagt    120
gatcccgccg gtgcgcaaaa agcagctgat actgtaaaag tagctggtgg tgacgctgtt    180
attgtccaag ctaatattgc gagcgaagct ggtgtggatg cattattagc tgcggccatt    240
gaccatttcg gtgacctaga tgtttgggtt aacaatgctg gtatggaaat aagtcacca     300 actcatgaag tctcattgga tgattggaat aaggtgacgg ctattgatca gaccggtgtg    360
ttccttggtt cacggacagc ccttgcgtac tttaaagcgc atcaaaagcc aggcaatatt    420
atcaacatgt catccgtaca cgaacggatt ccttggccaa cttttgcgag ctatgcagct    480
gctaagggga gtgtcaaact ctttactcag acgattgcta tggaatatgc gcaggacaat    540
attcgtgtga atgcaatcgg ccctggtgca atcaacacac caattaatgc tgaaaagttt    600
gccgatccac agcagtatga ccagaccgtt aacatggtgc aatgaaccg aatcgggacg     660 ccagaagagg ttgcagccgg agctgcttgg ctggcctcca gcgaatcaag ttatgtcacg    720
ggaattactt tatttattga tggcggtatg acactttatc ctgcatttaa ggatggtcaa    780
ggataa                                                               786
```

<210> SEQ ID NO 3
<211> LENGTH: 261
<212> TYPE: PRT
<213> ORGANISM: Lactobacillus pentosus

<400> SEQUENCE: 3

```
Met Tyr Glu Asp Leu Lys Gly Lys Thr Ala Val Ile Thr Gly Gly Ser
1               5                   10                  15

Lys Gly Ile Gly His Ala Ile Ala Glu Arg Phe Gly Gln Glu Gly Met
            20                  25                  30

Asn Val Val Ile Asn Tyr Asn Ser Asp Pro Ala Gly Ala Glu Ser Ala
        35                  40                  45

Val Ala Ser Val Glu Asn Lys Gly Gly His Ala Val Ala Val Gln Ala
    50                  55                  60

Asp Ile Ser Thr Glu Leu Gly Val Gln Ser Leu Leu Asp Ala Ala Val
65                  70                  75                  80

Glu Asn Phe Gly Asp Leu Asp Val Trp Ile Asn Asn Ala Gly Met Glu
                85                  90                  95

Ile Lys Ser Pro Thr His Glu Leu Ser Leu Asp Ala Trp Asn Lys Val
            100                 105                 110

Thr Ala Ile Asp Gln Thr Gly Val Phe Leu Gly Ser Arg Ile Ala Leu
        115                 120                 125

Ala Tyr Phe Lys Lys His Gly Lys Ala Gly Asn Ile Ile Asn Met Ser
    130                 135                 140

Ser Val His Glu Arg Ile Pro Trp Pro Thr Phe Ala Ser Tyr Ala Ala
145                 150                 155                 160

Ala Lys Gly Ser Val Lys Leu Phe Thr Gln Thr Ile Ala Met Glu Tyr
                165                 170                 175

Ala Lys Asp Asn Ile Arg Val Asn Ala Ile Gly Pro Gly Ala Ile Asn
            180                 185                 190

Thr Pro Ile Asn Ala Gln Lys Phe Ala Asp Lys Ala Gln Tyr Asp Gln
        195                 200                 205

Thr Val Lys Met Val Pro Met Asp Arg Ile Gly Asp Pro Glu Glu Val
    210                 215                 220

Ala Ala Gly Ala Ala Trp Leu Ala Ser Asn Glu Ser Ser Tyr Val Thr
225                 230                 235                 240

Gly Ile Thr Leu Phe Ile Asp Gly Gly Met Thr Leu Tyr Pro Ala Phe
                245                 250                 255

Lys Asp Gly Gln Gly
            260
```

<210> SEQ ID NO 4
<211> LENGTH: 786
<212> TYPE: DNA
<213> ORGANISM: Lactobacillus pentosus

<400> SEQUENCE: 4

```
atgtatgaag atttaaaagg taaaacagct gtcattactg gtggttctaa aggaattggt      60
catgccatcg ctgaaaggtt tggccaagag ggcatgaacg ttgtgattaa ctataacagt     120
gatccagctg gtgctgaatc agcggtagca agcgttgaaa ataaaggcgg tcatgctgtt     180
gcagttcaag ctgatattag tactgagcta ggggtgcagt ctttattaga tgctgcggtt     240
gagaattttg gtgatttgga tgtctggatc aataatgcgg ggatggagat taaatcaccg     300
acccatgagt taagcttaga tgcttggaat aaagtgacag caattgatca aaccggtgtg     360
ttcttgggtt cacgaattgc tttggcctat tttaagaagc acggtaaggc gggcaatatt     420
```

-continued

```
attaatatgt cttctgttca tgaacggatt ccttggccaa cttttgcgag ctatgcggca      480
gctaagggca gcgttaaact ttttacccaa actatcgcta tggaatatgc aaaggataat      540
attcgggtca atgcgattgg acctggtgca atcaatacac caattaacgc gcaaaaattt      600
gccgacaagg cgcaatatga tcagaccgta aaaatggttc cgatggatcg aattggtgat      660
ccggaagaag ttgctgctgg tgctgcttgg ttggcctcta acgaatcgag ttatgttacg      720
gggattaccc tctttattga tggtgggatg accctatacc ccgctttcaa agatggtcaa      780
ggttaa                                                                 786
```

<210> SEQ ID NO 5
<211> LENGTH: 20
<212> TYPE: DNA
<213> ORGANISM: Artificial
<220> FEATURE:
<223> OTHER INFORMATION: Primer 1
<220> FEATURE:
<221> NAME/KEY: misc_feature
<222> LOCATION: (3)..(3)
<223> OTHER INFORMATION: n represents a, t, g or c.
<220> FEATURE:
<221> NAME/KEY: misc_feature
<222> LOCATION: (12)..(12)
<223> OTHER INFORMATION: n represents a, t, g or c.
<220> FEATURE:
<221> NAME/KEY: misc_feature
<222> LOCATION: (15)..(15)
<223> OTHER INFORMATION: n represents a, t, g or c.

<400> SEQUENCE: 5
gtnaayaayg cnggnatgga                                                  20

<210> SEQ ID NO 6
<211> LENGTH: 20
<212> TYPE: DNA
<213> ORGANISM: Artificial
<220> FEATURE:
<223> OTHER INFORMATION: Primer 2
<220> FEATURE:
<221> NAME/KEY: misc_feature
<222> LOCATION: (3)..(3)
<223> OTHER INFORMATION: n represents a, t, g or c.
<220> FEATURE:
<221> NAME/KEY: misc_feature
<222> LOCATION: (15)..(15)
<223> OTHER INFORMATION: n represents a, t, g or c.

<400> SEQUENCE: 6
tcngcraayt tytyngcrtt                                                  20

<210> SEQ ID NO 7
<211> LENGTH: 42
<212> TYPE: DNA
<213> ORGANISM: Artificial
<220> FEATURE:
<223> OTHER INFORMATION: Primer 3

<400> SEQUENCE: 7
gagtgaagta catatgtatg aagatttaaa tggtaaggta gc                         42

<210> SEQ ID NO 8
<211> LENGTH: 42
<212> TYPE: DNA
<213> ORGANISM: Artificial
<220> FEATURE:
<223> OTHER INFORMATION: Primer 4

<400> SEQUENCE: 8
attcacgcat gcttattatc cttgaccatc cttaaatgca gg         42

<210> SEQ ID NO 9
<211> LENGTH: 42
<212> TYPE: DNA
<213> ORGANISM: Artificial
<220> FEATURE:
<223> OTHER INFORMATION: Primer 5

<400> SEQUENCE: 9
gagatttaaa catatgtatg aagatttaaa aggtaaaaca gc         42

<210> SEQ ID NO 10
<211> LENGTH: 42
<212> TYPE: DNA
<213> ORGANISM: Artificial
<220> FEATURE:
<223> OTHER INFORMATION: Primer 6

<400> SEQUENCE: 10
cttctaactg cagttattaa ccttgaccat ctttgaaagc gg         42

<210> SEQ ID NO 11
<211> LENGTH: 261
<212> TYPE: PRT
<213> ORGANISM: Pediococcus parvulus

<400> SEQUENCE: 11

Met Tyr Thr Asp Leu Glu Arg Lys Val Ala Val Ile Thr Gly Gly Ser
1               5                   10                  15

Lys Gly Ile Gly Asn Ala Ile Ala Thr Arg Phe Gly Gln Glu Lys Met
            20                  25                  30

Ala Val Val Val Asn Tyr Asn Ser Asp Pro Val Gly Ala Gln Lys Ala
        35                  40                  45

Ala Asp Gln Val Ile Ala Asn Cys Gly Lys Ala Val Ile Val Gln Ala
    50                  55                  60

Asn Val Ser Thr Glu Glu Gly Asn Gln Ala Leu Leu Gln Ala Ala Leu
65                  70                  75                  80

Asp Asn Phe Gly Asp Leu Asp Val Trp Val Asn Asn Ala Gly Met Glu
                85                  90                  95

Ile Lys Ser Ala Thr His Glu Leu Ser Leu Asp Ala Trp Asn Lys Val
            100                 105                 110

Val Ser Ile Asp Gln Thr Gly Val Phe Leu Gly Ser Lys Thr Ala Leu
        115                 120                 125

Ala Tyr Phe Lys Ala His Asn Lys Lys Gly Asn Ile Ile Asn Met Ser
    130                 135                 140

Ser Val His Glu Arg Ile Pro Trp Pro Thr Phe Ala Ser Tyr Ala Ala
145                 150                 155                 160

Ala Lys Gly Gly Val Lys Leu Phe Thr Gln Thr Ile Ala Met Glu Tyr
                165                 170                 175

Ala Lys Asp Gly Ile Arg Val Asn Ala Ile Gly Pro Gly Ala Ile Asn
            180                 185                 190

Thr Pro Ile Asn Ala Lys Lys Phe Ala Asp Lys Ala Gln Tyr Asp Gln
        195                 200                 205

Thr Val Ser Met Val Pro Met Asn Arg Ile Gly Thr Pro Glu Glu Val
    210                 215                 220

Ala Ala Gly Ala Ala Trp Leu Ala Ser Asp Glu Ser Ser Tyr Val Thr

```
                225                 230                 235                 240
Gly Ile Thr Leu Phe Ile Asp Gly Gly Met Thr Leu Tyr Pro Ala Phe
                    245                 250                 255
Lys Asp Gly Gln Gly
            260

<210> SEQ ID NO 12
<211> LENGTH: 786
<212> TYPE: DNA
<213> ORGANISM: Pediococcus parvulus

<400> SEQUENCE: 12
atgtatacag atttagagag aaaagtcgcg gttattactg gcggatctaa aggcattggg      60
aatgcgattg ctacccgttt tggtcaagaa aaaatggctg tcgtcgttaa ttataatagc     120
gatccggttg gggcacaaaa ggctgctgac caggtaattg caaattgtgg taaagctgtt     180
atcgtgcaag caaatgtttc tactgaagaa ggtaatcaag cattattaca agctgctcta     240
gataacttcg gcgacctaga tgtctgggtc aacaacgccg gtatggaaat caaatcagca     300
acccacgaac tttcattaga tgcttggaac aaagtcgttt ccattgacca aactggtgtc     360
ttcttgggat cgaagacagc gttagcttat ttcaaagctc acaataaaaa aggtaatatc     420
atcaatatgt catcggttca tgaacgaatt ccttggccaa catttgctag ttacgcagct     480
gcaaaaggtg gcgtaaagtt attcacgcaa acaattgcta tggaatacgc caaggatggt     540
atccgcgtca atgccattgg tcctggtgcc atcaacacgc caattaatgc taaaaaattc     600
gctgataaag cacaatatga tcaaacggtt tcaatggtgc caatgaatcg cattggtaca     660
ccggaagagg ttgccgccgg cgcagcttgg ctggcctctg acgaatcaag ttatgtgaca     720
ggcattacat tatttattga tggtgggatg actttatatc cagcatttaa ggatggtcaa     780
ggttaa                                                                 786

<210> SEQ ID NO 13
<211> LENGTH: 44
<212> TYPE: DNA
<213> ORGANISM: Artificial
<220> FEATURE:
<223> OTHER INFORMATION: Primer 7

<400> SEQUENCE: 13
gggggtactt catatgtata cagatttaga gagaaaagtc gcgg                       44

<210> SEQ ID NO 14
<211> LENGTH: 44
<212> TYPE: DNA
<213> ORGANISM: Artificial
<220> FEATURE:
<223> OTHER INFORMATION: Primer 8

<400> SEQUENCE: 14
taatttaagt cgacttatta accttgacca tccttaaatg ctgg                       44
```